United States Patent [19]

Behl

[11] Patent Number: 5,045,056
[45] Date of Patent: Sep. 3, 1991

[54] METHOD AND DEVICE FOR THERMAL ABLATION OF HOLLOW BODY ORGANS

[76] Inventor: Robert S. Behl, 361 Tioga Ct., Palo Alto, Calif. 94306

[21] Appl. No.: 407,839

[22] Filed: Sep. 15, 1989

[51] Int. Cl.⁵ .......................................... A61M 31/00
[52] U.S. Cl. .................................. 604/49; 604/113; 128/401
[58] Field of Search ............................. 604/113-114, 604/49; 128/399-401, 898

[56] References Cited

U.S. PATENT DOCUMENTS

| | | | |
|---|---|---|---|
| 3,901,224 | 8/1975 | Bucalo | 128/82.1 |
| 4,160,455 | 7/1979 | Law | 128/400 |
| 4,375,220 | 3/1983 | Matvias | 128/804 |
| 4,469,103 | 9/1984 | Barrett | 128/400 |
| 4,638,436 | 1/1987 | Badger et al. | 128/401 X |
| 4,676,258 | 6/1987 | Inokuchi et al. | 128/804 |
| 4,754,752 | 7/1988 | Ginsburg et al. | 604/113 X |
| 4,946,440 | 8/1990 | Hall . | |
| 4,979,948 | 12/1990 | Geddes et al. . | |

FOREIGN PATENT DOCUMENTS

| | | |
|---|---|---|
| 3725691 | 3/1988 | Fed. Rep. of Germany . |
| 281489 | 9/1970 | U.S.S.R. . |
| 1329781A2 | 8/1987 | U.S.S.R. . |

OTHER PUBLICATIONS

Coleman (1989) SCVIR, "Non-Surgical Ablation of the Gallbladder" pp. 214-221.
Getrajdman et al., (1985) Invest. Radiol. 20:393-398.
Becker et al., (1988) Radiology 167:63-68.
Salomonowitz et al., (1984) Arch. Surg. 119:725-729.
Getrajdman et al., (1986) Invest. Radiol. 21:400-403.
Remley et al., (1986) Invest. Radiol. 21:396-399.

Primary Examiner—John D. Yasko
Assistant Examiner—Corrine Maglione
Attorney, Agent, or Firm—Townsend and Townsend

[57] ABSTRACT

Hollow body organs, such as the gallbladder, may be ablated by introducing a substantially unheated thermally conductive medium to the interior of the organ. The thermally conductive medium is then heated to a temperature sufficient to necrose the endothelial lining or mucous membrane of the organ. After the lining or membrane has necrosed, the interior of the organ will fibrose over time and the organ will eventually be resorbed by the body. A catheter useful in performing the ablation method comprises an elongate member having a heating element at its distal tip. The catheter will include at least oen lumen for delivering the thermally conductive medium to the interior of the hollow body organ, and the heating means is used to raise the temperature of the thermally conductive medium after it has been delivered. Optionally, the catheter may include one or more inflatable balloons which facilitate sealing of the hollow body organ to inhibit leakage of the thermally conductive medium during the treatment process.

54 Claims, 5 Drawing Sheets

METHOD AND DEVICE FOR THERMAL ABLATION OF HOLLOW BODY ORGANS

BACKGROUND OF THE INVENTION

1. Field of the Invention

The present invention relates generally to methods and apparatus for the thermal ablation of hollow body organs, such as the gallbladder. In particular, the present invention relates to a catheter structure having a heating element at its distal end, where the catheter may be used to introduce an unheated thermally-conductive medium to the hollow body organ, and the heating element used to heat the medium in situ in order to destroy the endothelial lining or mucous membrane of the organ.

Heretofore, it has frequently been necessary to perform open surgery in order to remove diseased body organs, such as gallbladders, appendixes, and the like. For example, the current treatment for cholecystolithiasis (gallstone disease) involves the surgical removal of the gallbladder, referred to as a cholecystectomy. As with all major surgical procedures, the patient is exposed to the risk of trauma, infection, general anesthetic, as well as requiring extended recuperation time. It would therefore be desirable to provide for therapies for diseased organs which can effectively eliminate the organ without the necessity of open surgical intervention.

In recent years, a number of therapies have been developed as an alternative to open surgery, often referred to as "least invasive surgery." While least invasive surgical procedures have no fixed definition, they are generally characterized by the use of specialized surgical tools in combination with visual or radiographic imaging techniques. The specialized tool is generally inserted through an open body orifice or a small surgical incision, and the tool is then positioned within the body using the imaging technique to allow manipulation of the affected organ or structure. A common example of least invasive surgery is arthroscopic knee surgery where penetration of the surgical tools is minimal. Less accessible body organs, such as the heart and interior blood vessels, may be reached by specialized catheters which may be routed through the vascular system over relatively long distances. Typical of such vascular catheters are balloon dilatation catheters which are used to expand regions of stenosis within diseased blood vessels.

For the above reasons, it would be desirable to provide least invasive surgical methods and apparatus for the destruction or ablation of diseased hollow body organs, such as the gallbladder, the appendix, and the like. Such methods and apparatus should also be suitable for the treatment of relatively small body structures, such as blood vessels, and should be able to effect ablation without undue risk to surrounding body tissues and structures. In particular, the method and apparatus should be able to provide for the controlled application of thermal energy in order to destroy the hollow body organ with a minimal chance of regeneration.

2. Description of the Background Art

Coleman, Non-Surgical Ablation of the Gallbladder, Proc. 1988 SCVIR, pp 214–219, is a review article discussing various techniques for non-surgical gallbladder ablation, including the work of Salomonowitz and of Getrajdman relating to the introduction of an externally heated medium to induce fibrosis of the gallbladder. The article further presents data demonstrating thermal ablation of a dog's gallbladder after open surgical injection of hot contrast media. The work of Salomonowitz is described in Salomonowitz et al. (1984) Arch. Surg. 119:725–729. The work of Getrajdman is described in Getrajdman et al. (1985) Invest. Radiol. 20:393–398 and Getrajdman et al. (1986) Invest. Radiol. 21:400–403. The use of sclerosing agents to induce gallbladder fibrosis is described in Remley et al. (1986) Invest. Radiol. 21:396–399. See also Becker et al. (1988) Radiology 167:63–68. U.S. Pat. No. 4,160,455, describes a device for internally heating a body cavity for therapy, where the heat is intended to inhibit the growth of tumor cells. German Patent 37 25 691 describes a catheter combining a heater at its distal tip and a balloon proximate the heater, where the heater is not directly exposed to the fluid environment surrounding the catheter tip. Other patent documents describing heated or cooled catheters include U.S. Pat. Nos. 4,676,258; 4,638,436; 4,469,103; 4,375,220; 3,901,224; USSR 1329781-A; and USSR 281489.

SUMMARY OF THE INVENTION

The present invention is a method and apparatus for thermally ablating hollow body organs in order to induce fibrosis of the interior of the organ and eventual resorption of the organ by the body. The method relies on introducing a substantially unheated thermally conductive medium into the interior of the hollow body organ and subsequently heating the medium to a temperature sufficient to destroy the endothelial lining or mucous membrane. Use of an unconstrained media allows heat to be transferred effectively to a convoluted interior surface of the hollow body organ. Usually, all ducts, passages, and the like, opening into the hollow body organ will be blocked in order to inhibit leakage of the medium during the treatment procedure. The heating will be stopped after the desired thermal injury has occurred, and the thermally conductive medium may either be aspirated or left within the organ. The organ will subsequently fibrose and be resorbed over time.

The introduction of a substantially unheated thermally conductive medium minimizes the risk of injury to tissue, organs, and other body structures surrounding the hollow body organ being treated, as well as to medical personnel adminstering the treatment. The use of a radiologically detectable thermally conductive fluid such as contrast media allows visual confirmation that the medium is contained within the desired body organ and is not subject to leakage prior to heating of the medium.

The catheter of the present invention comprises an elongate member having proximal and distal ends with a heating means mounted near the distal end. The heating means is exposed to the fluid environment surrounding the distal end of the catheter and is thus able to directly heat the thermally conductive medium which has been introduced to the hollow body organ. Conveniently, the catheter includes a lumen or other means for introducing the thermally conductive medium. Thus, the catheter may be introduced into the interior of the hollow body organ and utilized both for introducing a thermally conductive medium and for heating the medium to ablate the lining of the organ. Usually, the catheter will also include one or more inflatable balloons for blocking ducts or other passages communicating with the hollow body organ. The catheter is introduced in such a way that the balloons are disposed within the ducts or passages and by then inflating the balloons, the desired sealing of the hollow body organ may be achieved.

DESCRIPTION OF THE SPECIFIC EMBODIMENTS

The present invention is useful for ablation of a wide variety of hollow body organs and body passages which have an endothelial lining, mucous membrane, or other internal surface which may be thermally injured to induce necrosis and subsequent fibrosis of the surrounding tissue. Exemplary hollow body organs include the gallbladder, the appendix, the uterus and the like. Exemplary hollow body passages include blood vessels, fistulas, and the like. Usually, the hollow body organs and body passages will be diseased or in some way abnormal prior to ablation according to the present invention. In some cases, however, it may be desirable to ablate and destroy apparently healthy body organs or parts in order to achieve a desired purpose, e.g., blockage of a blood vessel in a varicocele procedure. For convenience hereinafter, the phrase "hollow body organ" is intended to embrace both hollow body organs and hollow body passages.

The method of the present invention relies on introducing a thermally conductive medium into the interior of the hollow body organ in such a way that the organ is filled with the medium and the medium is in good thermal contact with substantially the entire interior surface of the organ. In this way, by heating the medium as will be described hereinafter, the temperature of the endothelial lining or mucous membrane of the body organ can be raised to a preselected temperature for a preselected minimum time period in order to permanently injure the lining and subsequently induce necrosis The thermally conductive medium can be virtually any physiologically-compatible liquid, solution, slurry, gel, and the like, which may be percutaneously or directly introduced into the interior of the hollow body organ. Exemplary thermally conductive media include water, saline, contrast medium, physiological irrigating solution, and the like.

The thermally conductive medium will be introduced to the interior of the hollow body organ at a temperature below that which will have a deleterious effect on the tissue and organ surrounding the hollow body organ being treated. The temperature will be below about 60° C., usually being below about 50° C., and more usually being at body temperature (37° C.) or room temperature (about 20° C.). In some cases, however, it may be desirable to introduce the contrast medium above body temperature, usually in the range from about 37° C. to 50° C., in order to shorten the time necessary to raise the temperature of the medium to the treatment temperature, discussed hereinafter.

In order to induce necrosis of the endothelial lining or mucous membrane of the hollow body organ, the temperature of the thermally conductive medium will be raised above a threshold level which results in injury to the endothelial lining or mucous membrane. The threshold temperature will generally be above 60° C., usually being in the range from 60° C. to 120° C., more usually being in the range from 65° C. to 100° C., and preferably being in the range from about 70° C. to 90° C. Depending on the precise temperature employed and on the nature of the particular organ being treated, the thermally conductive medium will be maintained above the threshold temperature for a period of time in the range from about 1 to 60 minutes, usually being in the range from about 1 to 30 minutes, more usually being in the range from about 2 to 20 minutes, and preferably being in the range from about 2 to 10 minutes. Usually, the temperature of the thermally conductive medium will be raised as rapidly as possible and maintained at a substantially constant treatment temperature for the desired treatment period. Alternatively, the treatment temperature may be varied during the treatment period with the total treatment time being adjusted to take the variation in temperature into account.

After the hollow body organ has been treated with the heated thermally conductive medium at a temperature and for a time sufficient to induce necrosis of the endothelial lining or mucous membrane of the organ, the thermal energy being delivered to the medium will be terminated. The thermally conductive medium may then be aspirated from the hollow body organ, typically using the same catheter which was employed to deliver the medium and raise the temperature of the medium as described above. Usually, however, the thermally conductive medium will not be aspirated until the temperature has decreased sufficiently so that its withdrawal will not expose tissues and organs surrounding the catheter to risk. Normally the withdrawal temperature will be below about 55° C., preferably being below about 45° C. Alternatively, the thermally conductive medium can be left within the hollow body organ where it will be resorbed or eliminated by normal physiological processes.

The catheter of the present invention comprises an elongate member having proximal and distal ends. The elongate member may be flexible or rigid, although flexible catheters are preferred for most applications. The length of the catheter will vary depending on the application with short, rigid catheters typically having a length in the range from about 10 to 20 cm, and long flexible catheters typically having a length in the range from about 20 to 40 cm. Rigid elongate members may be formed from metals, typically stainless steel, rigid plastics, and the like, while flexible elongate members will typically be formed from extruded organic polymers, such as silicone rubber, polyurethane, polyvinyl chloride, nylon, and the like. Elongate members will typically include a multiplicity of lumens to provide for fluid communication between the proximal end (outside the patient) to the distal end (inside the patient). Normally, a lumen will be provided for delivering and/or aspirating the thermally conductive medium to the hollow body organ. Additional lumens may be provided for inflation of one or more balloons, for delivery of the catheter over a movable guidewire, for venting the hollow body organ while the thermally conductive medium is being delivered, and the like.

A heating means for raising the temperature of the fluid environment surrounding the distal end of the catheter will be provided at or near the distal tip of the elongate member typically being within about 10 cm, more typically being within about 5 cm. The heating means will generally provide a heated surface for convectively heating fluid surrounding the catheter tip, typically comprising a resistive heater, a radiating block heated by laser energy, or the like. The heating means may also comprise a microwave emitter capable of heating the fluid directly or a radiofrequency heating element. In some cases, it may also be possible to heat the thermally conductive medium using dispersed laser radiation. In that case, it will be desirable to color or dye the thermally conductive medium so that it can absorb radiation at the wavelength of the laser source.

A system will be provided for controlling the temperature to which the thermally conductive medium is heated by the heating means. Such a temperature control system may comprise a feedback controller where a temperature sensing element (typically a thermocouple or thermistor) is mounted on the catheter at a location chosen to accurately measure the heated environment surrounding the catheter, and the energy delivered to the heating means is regulated based on the measured temperature of the medium. Alternatively, numerous autoregulating heaters are available which do not require a separate control loop.

Usually, the catheter will include at least one inflatable balloon for occluding a duct or passage which would otherwise allow drainage of the thermally conductive medium from the hollow body organ during the course of the treatment. At least one balloon will generally be located at the distal tip of the elongate member of the catheter and will be inflatable through an inflation lumen running through the catheter from the distal to the proximal end thereof. For many applications it will be desirable to inflate the occluding balloon with a thermally conductive medium, frequently the same medium used to fill the hollow body organ, so that the area in contact with the balloon will be heated and necrosed. Optionally, means for heating the medium within the balloon to a temperature sufficient to induce necrosis in the endothelial lining or mucous membrane surrounding the inflated balloon may be provided. Alternatively, a thermally insulating medium such as carbon dioxide may be used to inflate the balloon when it is desired to protect the surrounding tissue and organs.

One or more additional inflatable balloons may also be provided in order to seal other passages communicating with the hollow body organ. For example, a second inflatable balloon spaced proximally from the first on the other side of the heating element may be provided. The first and second balloons may then be used to define a volume to be treated therebetween. Other balloon configurations may also be used for trapping the thermal media in a particular hollow body organ or portion of a hollow body organ.

Referring now to FIGS. 1-4, a catheter 10 comprises an elongate flexible body 12 having a proximal end 14 and a distal end 16. The elongate member 12 includes a plurality of axial slots 18 formed at or near the distal end 16 and a heating element 20 disposed within the slots. The heating element 20 is of a type which provides a heated external surface, typically being a resistive heating element where a pair of wires 22 are run from the heating element to the proximal end 14 of the catheter where they are taken out through a sealed port 23 in a proximal housing 24. The wires 22 will typically be run through a central lumen 26 and will be connected to a suitable power supply (not shown) for heating the heating element 20 to a desired temperature.

Figure 2:
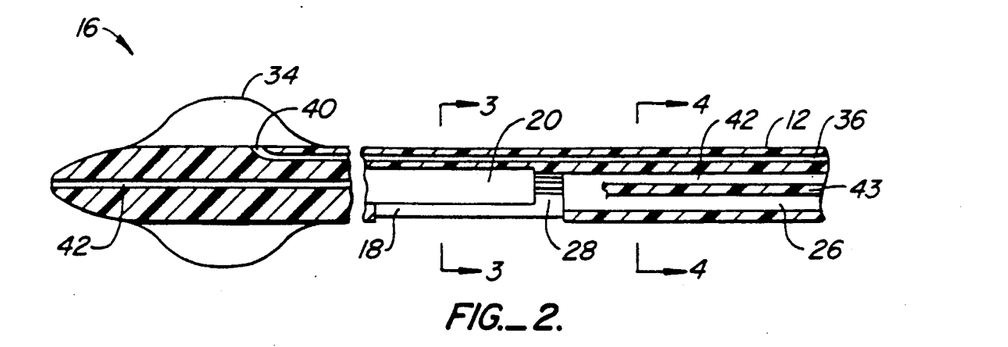
FIG. 2 is a detailed elevational view of the distal end of the catheter of FIG. 1 shown in crosssection.
Figure 3:
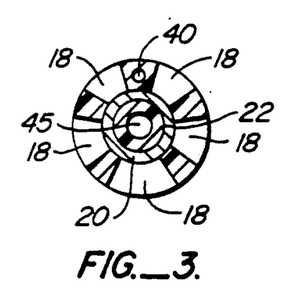
FIG. 3 is a cross-sectional view taken along line 3—3 of FIG. 2.
Figure 4:
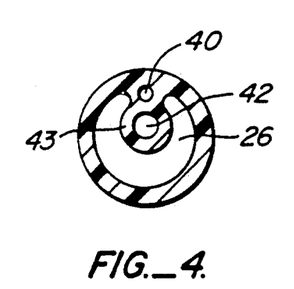
FIG. 4 is a cross-sectional view taken along line 4—4 of FIG. 2.

The central lumen 26 extends from the proximal end 14 of the elongate member 12 and terminates at the proximal end of heating element 20 (FIG. 2). A plurality of radial passages 28 (FIG. 2) are provided between the distal end of the central lumen 26 and the proximal end of the heater 20, which passages open into the axial slots 18. The proximal end of central lumen 26 is connected through a side port 30 on the proximal housing 24. In this way, thermally conductive medium may be delivered through the central lumen 26 past the heating surface of heating element 20 and into the hollow body organ. The thermally conductive media is thus rapidly heated as it passes the heater 20 into the hollow body organ.

Figure 1:
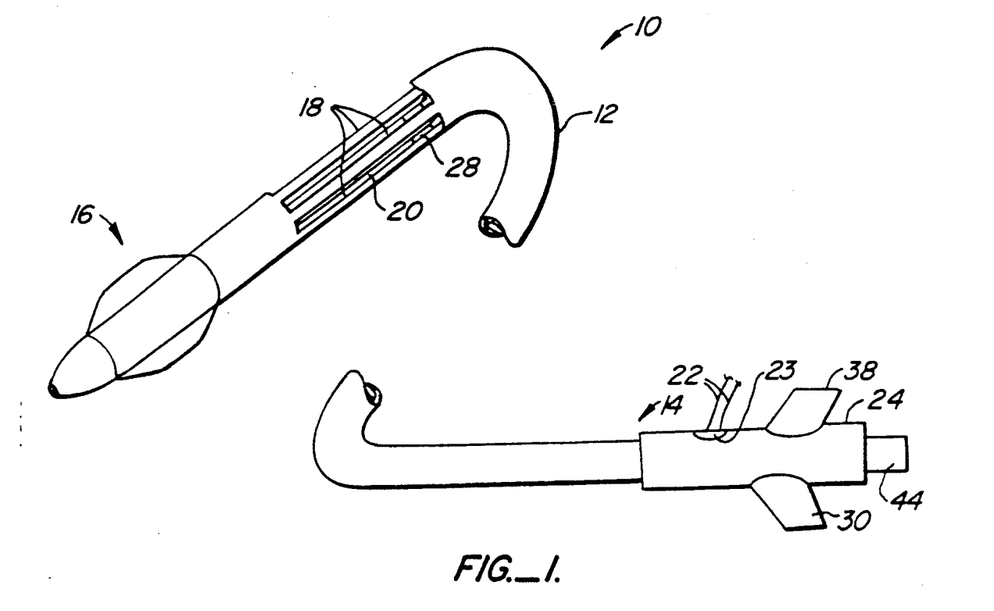
FIG. 1 is a perspective view of a thermal ablation catheter constructed in accordance with the principles of the present invention.

The catheter 10 also includes an inflatable balloon 34 at its distal tip. The balloon 34 may be inflated through inflation lumen 36 which extends from an inflation port 38 on housing 24 to an outlet port 40 communicating directly with the interior of the balloon 34. The balloon 34 will usually be inflated with a heat conductive medium which will be heated by conduction from the heated fluid trapped by the balloon within the hollow body organ. An optional system (not illustrated) for heating the balloon within the medium may be provided. Systems for heating inflation medium within a balloon are described in U.S. Pat. No. 4,754,752, the disclosure of which is incorporated herein by reference.

A third lumen 42 is formed in a tubular extension 43 disposed in central lumen 26. Lumen 42 extends through the distal tip of the catheter 10 and is axially-aligned with a lumen 45 (FIG. 3) through the heater 22. The tubular extension 43 is usually separated from the main portion of flexible body 12 and attached to the heater (not illustrated) to allow thermally conductive fluid to flow unobstructed from the central lumen 26 past the heater 22 and through the slots 18. Together, the lumens 42, 43, and 45 are intended to form a fluid tight passage which can receive a movable guidewire which can be used to facilitate placement of the catheter 10 within the desired hollow body organ, as described in more detail hereinafter.

Figure 5:
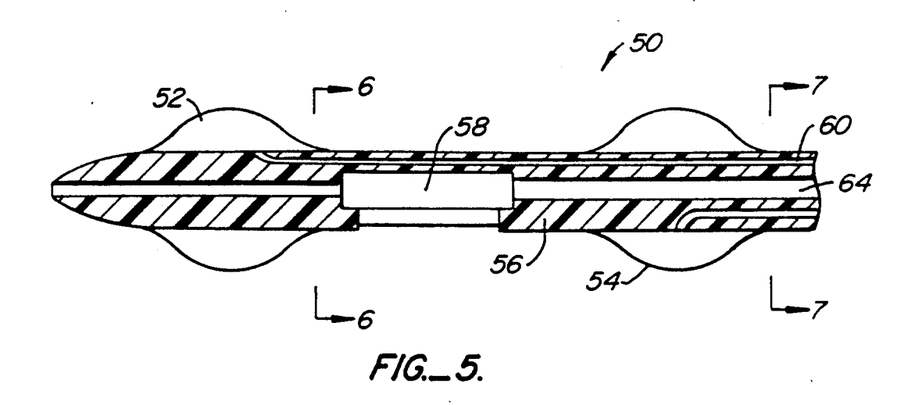
FIG. 5 is a detailed elevational view of the distal end of the catheter having two inflation balloons spaced-apart at its distal end shown in cross-section.
Figure 6:
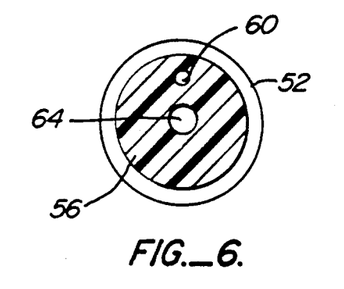
FIG. 6 is a cross-sectional view taken along line 6—6 of FIG. 5.
Figure 7:
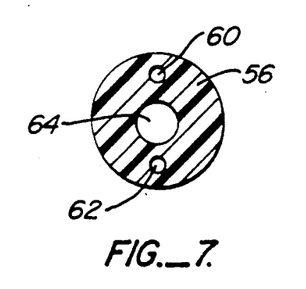
FIG. 7 is a cross-sectional view taken along line 7—7 of FIG. 5.

Referring now to FIGS. 5-7, a catheter 50 which is similar to catheter 10 but includes a pair of spaced-apart inflation balloons 52 and 54 is illustrated. The catheter 50 includes an elongate flexible member 56, a heating element 58, and is generally constructed as described previously for catheter 10. The catheter 50, however, includes the second inflatable balloon 54 which is spaced-apart proximally from the first balloon 52, with the two balloons being disposed on opposite sides of heating element 58. In this way, the two balloons 52 and 54 are able to isolate a volume therebetween which includes the heater 58. By introducing the thermally conductive medium between the two balloons 52 and 54, the heater 58 may then be used to heat the isolated medium in treating a desired portion of a hollow body organ. The catheter 50 includes first inflation lumen 60 to inflate the first balloon 52 and a second inflation lumen 62 to inflate the second balloon 54. A central lumen 64 serves both to introduce thermally conductive medium and to receive a guidewire to facilitate placement of the catheter. The guidewire may be received in a tubular extension (not illustrated) or a seal, such as an O-ring, may be provided to inhibit leakage of medium.

Referring now to FIGS. 8A-8H, the use of a two-balloon catheter of the type illustrated in FIG. 5 for ablating a gallbladder will be described. Gallbladder ablation will be desirable in cases of cholecystolithiasis where the diseased gallbladder is likely to continue production of gall stones. Gallbladder ablation according to the present invention will generally be performed after the removal of gall stones by established least invasive procedures, typically by either percutaneous cholecystostomy or by lithrotriptor.

Figure 8A:
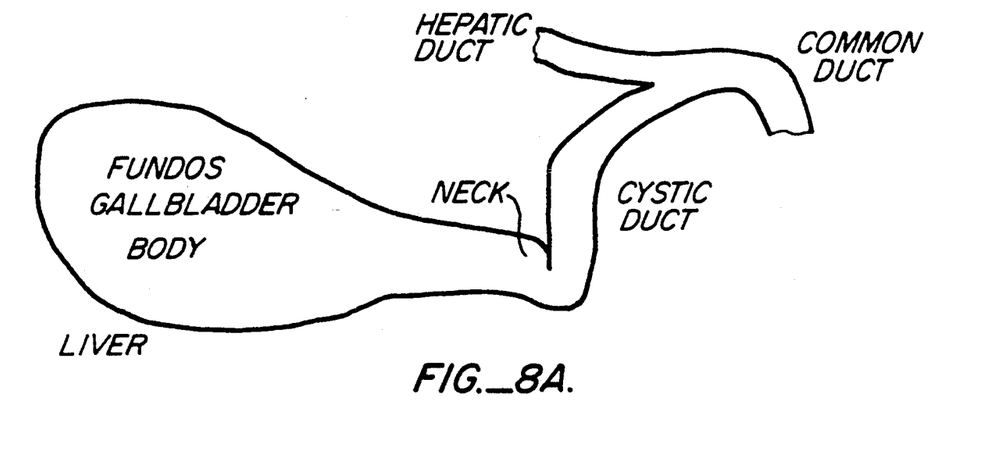
FIGS. 8A-8H illustrate the method of the present invention used in the thermal ablation of a gallbladder.
Figure 8B:
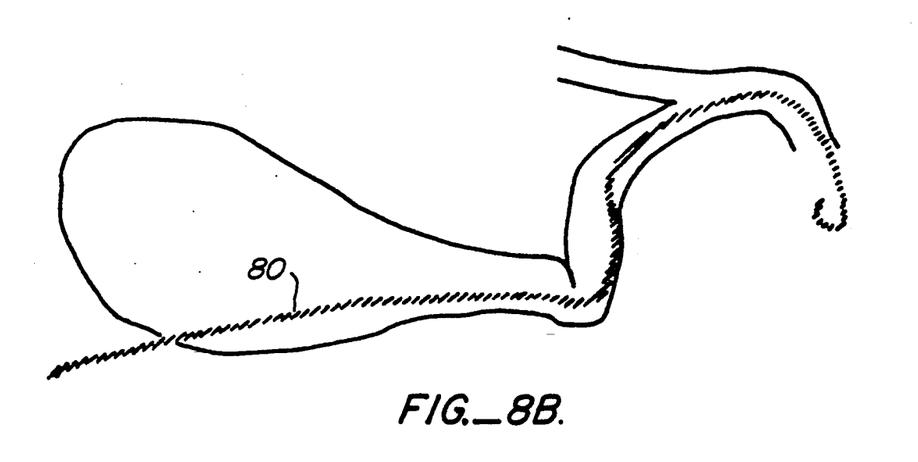
Figure 8C:
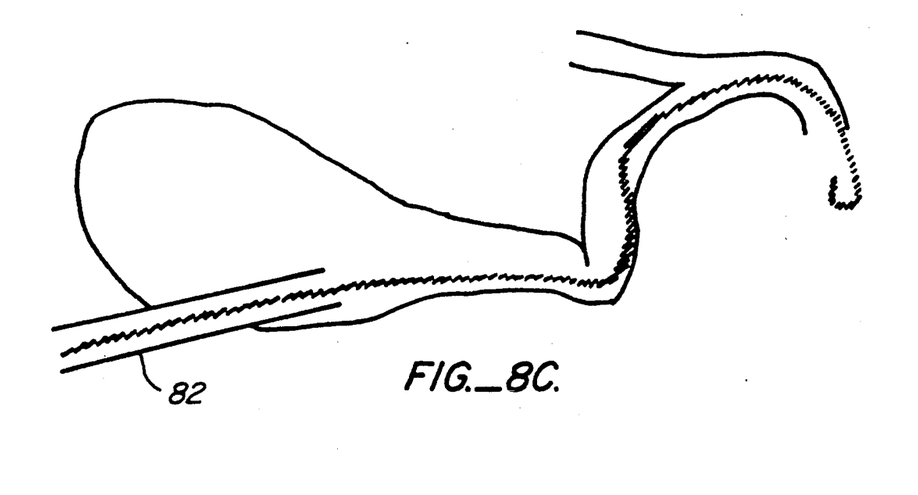

The intact gallbladder is illustrated in FIG. 8A and includes a hollow sac structure connected to the cystic duct through the neck of the gallbladder. The cystic duct, in turn, is connected to the hepatic duct and common bile duct. The gallbladder is located on the lower (inferior) surface of the liver in a hollow (fossa) beneath the right lobe. The upper (superior) surface of the gallbladder is attached to the liver by connective tissue.

Figure 8D:
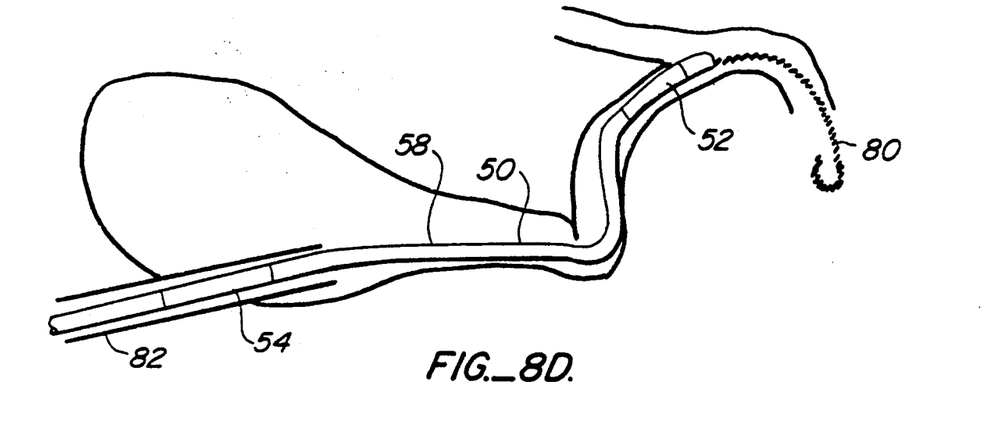

In treating the gallbladder according to the method of the present invention, a percutaneous guidewire 80 (FIG. 8B) is inserted into the gallbladder through the trans-hepatic route and into the common bile duct. A sheath 82 (FIG. 8C) is then placed over the guidewire 80 to provide for access into the interior of the organ. The catheter 50 may then be inserted over the guidewire 80 and positioned so that the first balloon 52 lies beyond the neck of the gallbladder and just proximal to the junction between the hepatic duct and the common duct 50 (FIG. 8D). The second balloon 54 will remain within the sheath 82, while the heater 58 is located within the main body of the gallbladder.

Figure 8E:
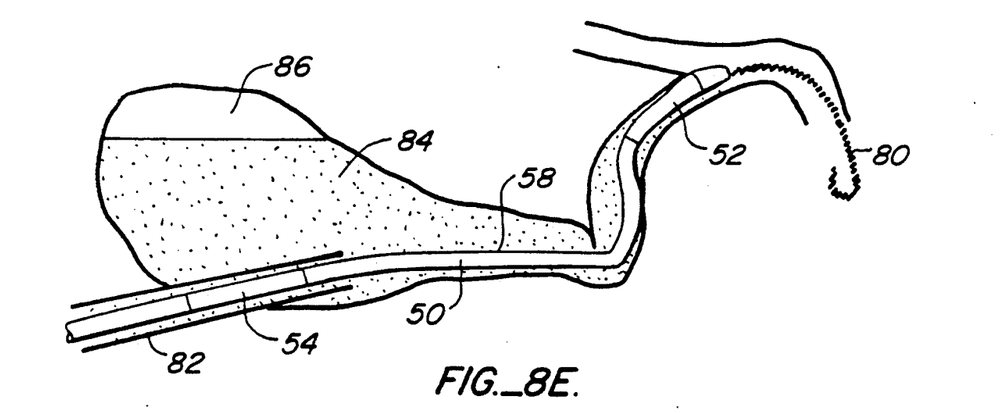
Figure 8F:
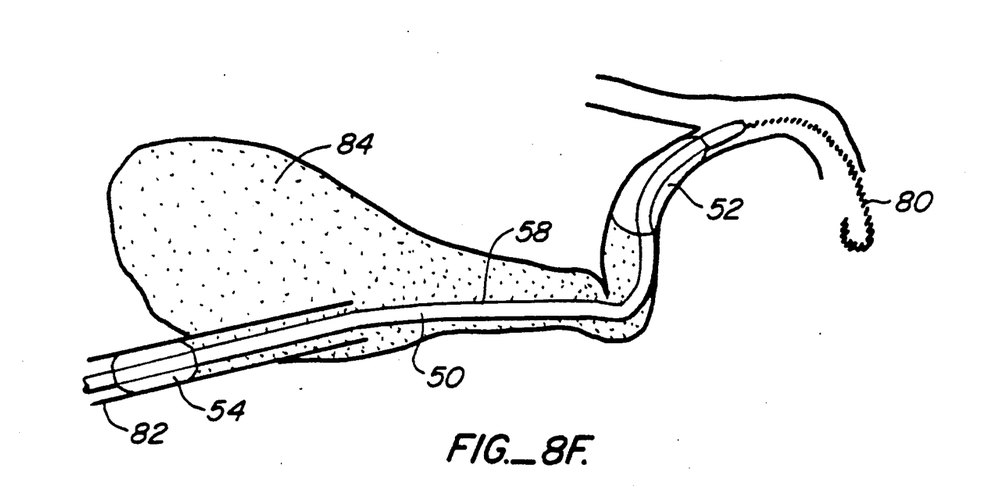

After the catheter 50 is in place, the thermally conductive medium 84 is introduced into the interior of the gallbladder through the catheter (FIG. 8E). The medium 84 is introduced until the main sac is entirely filled, as illustrated in FIG. 8F, and the first and second balloons 52 and 54 are inflated in order to inhibit loss of the medium through the cystic duct and the sheath 82. During the introduction of the thermally conductive medium to the gallbladder, it may be necessary to adjust the position of the patient in order to expel trapped gases 86 (FIG. 8E). The gases 86 may be released through either the cystic duct or the sheath 82, or may be vented through a specially provided vent (not illustrated) within the catheter 50.

Figure 8G:
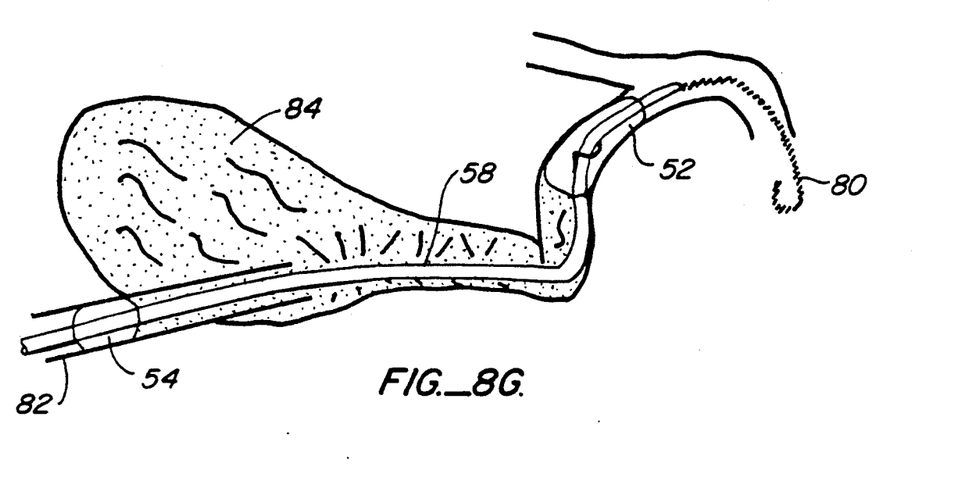

Once the main sac of the gallbladder is completely filled with thermally conductive medium 84 (which may be confirmed by fluoroscopic examination of a radiopaque medium), the heating element 58 will be activated to raise the temperature of the medium, either by convection, radiation, or high frequency heating (FIG. 8G). Optionally, the thermally conductive medium 84 may have been partially heated by the heating element 58 as the medium is introduced by the catheter 50. Heat will be conducted from the interior of the organ through the thermally conductive media in the first balloon 52 in order to necrose the mucosa of the cystic duct in order to assure that the gallbladder lining will not regenerate. Usually, the second balloon 54 will be inflated with a thermally insulating medium to protect the liver from the heat of the medium 84.

After maintaining the temperature of the heat conductive medium 84 (and optionally the inflation medium with balloon 52) at the desired ablation temperature for a sufficient time to completely necrose the mucosa of the gallbladder, the heating element 58 may be deenergized.

Figure 8H:
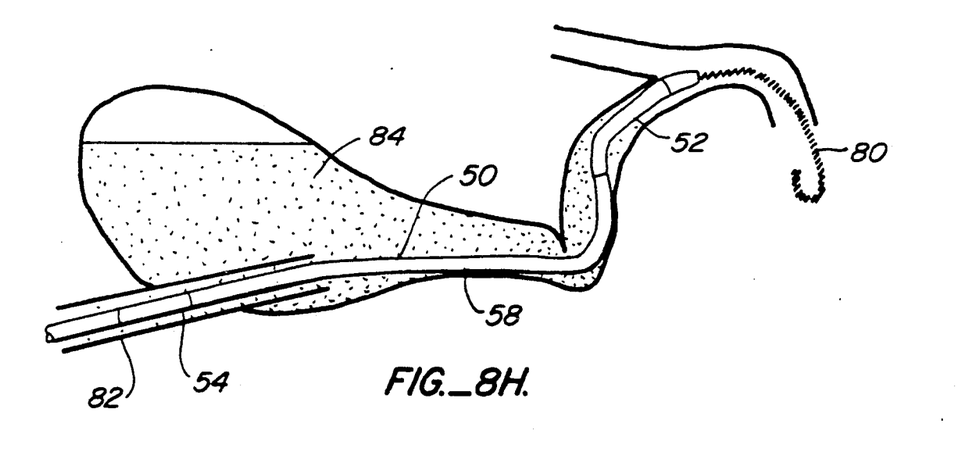
Figure 9:
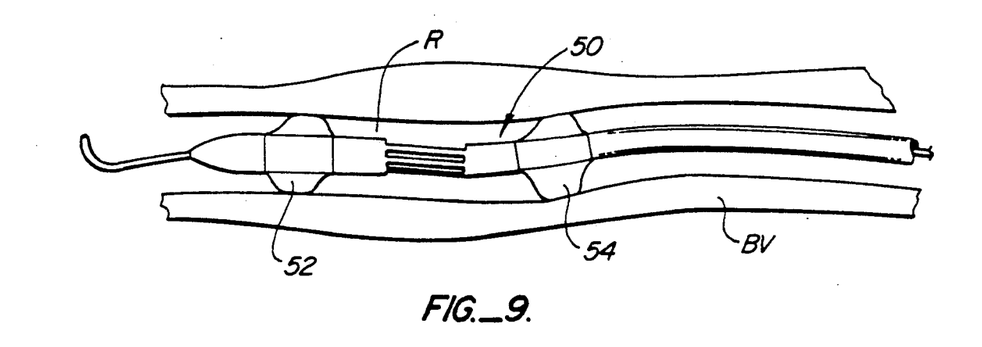
FIG. 9 illustrates the method of the present invention used in the thermal ablation of a segment of a blood vessel.

After allowing cooling, the thermally conductive medium 84 may be aspirated through the catheter or optionally through the sheath 82 after balloon 54 has been deflated (FIG. 8H). Alternatively, the thermally conductive medium 84 may be left within the main sac of the gallbladder from which it will eventually drain through the cystic duct and be eliminated by normal physiologic processes.

After about six weeks, the endothelial lining of the gallbladder will be completely necrotic. The inflammation process will completely replace the lining of the gallbladder with fibrotic tissue within about twelve weeks and the organ will start to resorb.

Although the foregoing invention has been described in detail for purposes of clarity of understanding, it will be obvious that certain modifications may be practiced within the scope of the appended claims.

What is claimed is:

1. A method for ablating a hollow body organ, said method comprising:
    introducing into the hollow body organ a substantially unheated thermally conductive medium, wherein said medium is generally unconstrained so that it is in direct contact with the interior of the hollow body organ; and
    heating the thermally conductive medium within the hollow body organ to a temperature and for a time sufficient to destroy the lining of said organ, whereby said organ will subsequently fibrose and be resorbed over time.

2. A method as in claim 1, wherein the thermally conductive medium is heated to a temperature in the range from about 60 to 120° C.

3. A method as in claim 2, wherein the temperature is maintained within said range for a period of time in the range from about 1 to 60 minutes.

4. A method as in claim 3, wherein heating of the thermally conductive medium is stopped after said period of time.

5. A method as in claim 4, wherein the thermally conductive medium is allowed to remain in said hollow body organ after the heating is stopped.

6. A method as in claim 4, wherein the thermally conductive medium is aspirated from said hollow body organ after the heating is stopped.

7. A method as in claim 1, wherein at least one drainage path from the hollow body organ is blocked to inhibit loss of the thermally conductive medium prior to heating said medium.

8. A method as in claim 7, wherein the hollow body organ is a gallbladder and the cystic duct is blocked to inhibit loss of fluid.

9. A method as in claim 7, wherein the hollow body organ is a blood vessel having a lumen, wherein the lumen is blocked in an upstream and a downstream location to inhibit loss of fluid from a region therebetween.

10. A method as in claim 1, wherein the thermally conductive medium is convectively heated.

11. A method as in claim 1, wherein the thermally conductive medium is radiantly heated.

12. A method as in claim 1, wherein the thermally conductive medium is selected from the group consisting of water, saline, contrast medium, and physiological irrigating solution.

13. A method for ablating a hollow body organ, said method comprising:
percutaneously introducing a catheter into the interior of said hollow body organ, said catheter having proximal and distal ends and including a heating means at or near its distal end;
introducing a substantially unheated thermally conductive medium through the catheter to the interior of said hollow body organ, wherein said medium is generally unconstrained so that it is in direct contact with the interior of the hollow body organ;
heating the thermally conductive medium within the hollow body organ using the heating means on the catheter to a temperature sufficient to destroy the lining of said organ, whereby said organ will subsequently fibrose and be resorbed over time.

14. A method as in claim 13, wherein the thermally conductive medium is heated to a temperature in the range from about 60 to 120° C.

15. A method as in claim 14, wherein the temperature is maintained within said range for a period of time in the range from about 1 to 60 minutes.

16. A method as in claim 15, wherein heating of the thermally conductive medium is stopped after said period of time.

17. A method as in claim 16, wherein the thermally conductive medium is allowed to remain in said hollow body organ after the heating is stopped.

18. A method as in claim 16, wherein the thermally conductive medium is aspirated from said hollow body organ after the heating is stopped.

19. A method as in claim 13, further comprising inflating a balloon proximate the distal end of the catheter to block at least one drainage path from the hollow body organ to inhibit loss of the thermally conductive medium prior to heating said medium.

20. A method as in claim 19, wherein the hollow body organ is a gallbladder and the balloon is inflated in the cystic duct.

21. A method as in claim 13, further comprising inflating at least two balloons spaced-apart from each other on opposite sides of the heating means proximate the distal end of the catheter to isolate a region within the hollow body organ prior to heating the thermally conductive medium within said region.

22. A method as in claim 21, wherein the hollow body organ is a blood vessel and two balloons are inflated to block upstream and downstream locations within said blood vessel.

23. A method as in claim 13, wherein the heating means is a resistive heating element and the thermally conductive medium is heated by passing current through said resistive heating element.

24. A method as in claim 13, wherein the heating means is a coil and the thermally conductive medium is heated by applying a radiofrequency current thereacross.

25. A method as in claim 13, wherein the heating means is a radiofrequency or a microwave radiation generator and the thermally conductive medium is heated by passing the radiation therethrough.

26. A method as in claim 13, wherein the thermally conductive medium is capable of absorbing radiant energy at preselected wavelengths and the heating means includes an optical waveguide, wherein said medium is heated by supplying radiation within said preselected wavelengths through said optical waveguide.

27. A method as in claim 19, further comprising heating an inflation medium within the balloon to a temperature sufficient to destroy the lining of the hollow body organ in contact with the balloon.

28. A method as in claim 21, further comprising heating an inflation medium within at least one of the balloons to a temperature sufficient to destroy the endothelial lining of the hollow body organ in contact with said at least one balloon.

29. A method as in claim 19, wherein the balloon is inflated with a thermally insulating medium to inhibit conduction of heat from the thermally conductive medium.

30. A method as in claim 21, wherein at least one of the balloons is inflated with a thermally insulating medium to inhibit conduction of heat from the thermally conductive medium.

31. A method for thermally ablating a gallbladder, said method comprising the following steps performed in a preselected order:
sealing the cystic duct to inhibit leakage from the gallbladder;
introducing a substantially unheated thermally conductive medium into the gallbladder; and
heating the thermally conductive medium within the gallbladder to a temperature and for a time period sufficient to induce fibrosis of the of the gallbladder.

32. A method as in claim 31, wherein the cystic duct is sealed prior to introducing the unheated thermally conductive medium.

33. A method as in claim 31, wherein the unheated thermally conductive medium is introduced at least in part before the cystic duct is sealed.

34. A method as in claim 31, wherein the thermally conductive medium is at least partially heated as it is introduced.

35. A method as in claim 31, wherein the thermally conductive medium is heated to a temperature in the range from about 60 to 120° C.

36. A method as in claim 35, wherein the temperature is maintained within said range for a period of time in the range from about 1 to 60 minutes.

37. A method as in claim 36, wherein heating of the thermally conductive medium is stopped after said period of time.

38. A method as in claim 37, wherein the thermally conductive medium is allowed to remain in said hollow body organ after the heating is stopped.

39. A method as in claim 37, wherein the thermally conductive medium is aspirated from said hollow body organ after the heating is stopped.

40. A method as in claim 31, wherein the thermally conductive medium is convectively heated.

41. A method as in claim 31, wherein the thermally conductive medium is radiantly heated.

42. A method as in claim 31, wherein the thermally conductive medium is selected from the group consisting of water, saline, contrast medium, and physiological irrigating solution.

43. A method for thermally ablating a gallbladder, said method comprising:

percutaneously introducing a catheter into the interior of the gallbladder, said catheter having proximal and distal ends and including a heating means and an inflation balloon at its distal end;

followed by the following steps performed in a preselected order:

introducing a substantially unheated thermally conductive medium through the catheter to the interior of the gallbladder;

inflating the balloon to seal the cystic duct to inhibit leakage of the thermally conductive medium from the interior of the gallbladder; and heating the thermally conductive medium within the interior of the gallbladder using the heating means on the catheter to a temperature sufficient to destroy the mucosa of the gallbladder, whereby the gallbladder will subsequently fibrose and be resorbed over time.

44. A method as in claim 43, wherein the thermally conductive medium is heated to a temperature in the range from about 60 to 120° C.

45. A method as in claim 44, wherein the temperature is maintained within said range for a period of time in the range from about 1 to 60 minutes.

46. A method as in claim 45, wherein heating of the thermally conductive medium is stopped after said period of time.

47. A method as in claim 46, wherein the thermally conductive medium is allowed to remain in said gallbladder after the heating is stopped.

48. A method as in claim 43, further inflating a second inflatable balloon located on the catheter proximally of the heating means to seal an entry passage formed through the gallbladder to permit introduction of the catheter.

49. A method as in claim 48, wherein the second inflatable balloon is inflated with a thermally insulating medium to protect the liver.

50. A method as in claim 43, wherein the heating means is a resistive heating element and the thermally conductive medium is heated by passing current through said resistive heating element.

51. A method as in claim 43, wherein the heating means is a coil and the thermally conductive medium is heated by applying a radiofrequency current thereacross.

52. A method as in claim 43, wherein the heating means is a microwave generator and the thermally conductive medium is heated by emitting microwave energy therefrom.

53. A method as in claim 43, wherein the thermally conductive medium is capable of absorbing radiation at preselected wavelengths and the heating means includes an optical waveguide, wherein said medium is heated by supplying radiation within said preselected wavelengths through said optical waveguide.

54. A method as in claim 43, further comprising heating an inflation medium within the inflatable balloon to a temperature sufficient to destroy the lining of the hollow body organ.

* * * * *